US009110032B2

(12) United States Patent
Farley, III et al.

(10) Patent No.: US 9,110,032 B2
(45) Date of Patent: Aug. 18, 2015

(54) SYSTEM AND METHODS FOR INSPECTING TIRE WHEEL ASSEMBLIES

(71) Applicant: INTEGRO TECHNOLOGIES CORP., Salisbury, NC (US)

(72) Inventors: Edwin Starke Farley, III, Spartanburg, SC (US); Drew Waller, Davidson, NC (US); Shawn A. Campion, Salisbury, NC (US); Gerald Ross Van Dam, Franklin, TN (US); Shankar Jagadeesan, Santa Clara, CA (US)

(73) Assignee: INTEGRO TECHNOLOGIES CORP., Salisbury, NC (US)

( * ) Notice: Subject to any disclaimer, the term of this patent is extended or adjusted under 35 U.S.C. 154(b) by 44 days.

(21) Appl. No.: 14/052,646

(22) Filed: Oct. 11, 2013

(65) Prior Publication Data

US 2014/0270466 A1 Sep. 18, 2014

Related U.S. Application Data

(60) Provisional application No. 61/783,722, filed on Mar. 14, 2013.

(51) Int. Cl.
*G06K 9/00* (2006.01)
*G01N 21/88* (2006.01)

(52) U.S. Cl.
CPC ..................... *G01N 21/88* (2013.01)

(58) Field of Classification Search
None
See application file for complete search history.

(56) References Cited

U.S. PATENT DOCUMENTS

| 4,839,914 A | * | 6/1989 | Curry | 378/61 |
| 8,542,881 B2 | * | 9/2013 | Teti et al. | 382/104 |
| 2011/0069323 A1 | * | 3/2011 | Takahashi et al. | 356/625 |
| 2013/0202156 A1 | * | 8/2013 | Joly et al. | 382/104 |
| 2014/0232852 A1 | * | 8/2014 | Nobis et al. | 348/128 |
| 2014/0283591 A1 | * | 9/2014 | Takahashi et al. | 73/146 |

* cited by examiner

*Primary Examiner* — Chan Park
*Assistant Examiner* — Mia M Thomas
(74) *Attorney, Agent, or Firm* — Tillman Wright, PLLC; Neal Wolgin; Jeremy C. Doerre

(57) ABSTRACT

A system includes a tire inspection station configured to inspect a tire of a tire wheel assembly. The tire inspection station includes a lifting assembly configured to lift and rotate a tire wheel assembly disposed in the tire inspection station, movable centering arms adjustably positionable to center a hub of a tire wheel assembly relative to the lifting assembly, and top and bottom camera assemblies configured to image sidewalls of the tire wheel assembly when it is lifted. The system further includes software configured to process images from the camera assemblies and display results of the processing. The system additionally includes a wheel inspection station comprising a camera. The system further includes software configured to process images from the camera to verify wheel properties.

12 Claims, 17 Drawing Sheets

SYSTEM AND METHODS FOR INSPECTING TIRE WHEEL ASSEMBLIES

CROSS-REFERENCE TO RELATED APPLICATION

The present application is a U.S. nonprovisional patent application of, and claims priority under 35 U.S.C. §119(e) to, U.S. provisional patent application Ser. No. 61/783,722, filed Mar. 14, 2013, which provisional patent application is incorporated by reference herein. The present application further incorporates herein by reference the entire disclosure of Appendices A-D attached hereto.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to systems and methods for inspecting tires, wheels, and tire wheel assemblies. The system of the present invention may be used in any number of applications, including, without limitation, to inspect a tire wheel assembly ("TWA") prior to shipment of the TWA to an automobile manufacturer.

A need exists for an improved way for suppliers of tire-wheel assemblies to inspect the TWAs prior to shipment to a customer. In the past, automobile manufacturers were very heavily vertically integrated. As such, they would manufacture as many parts as they deemed reasonable to control their supply chain, allowing them to insulate themselves from parts shortages and price volatility. While tires have traditionally been manufactured by dedicated suppliers, auto wheels were frequently manufactured by the auto manufacturer. Automobile manufacturers have largely moved away from shipping autos with simple steel wheels to shipping autos with higher performance magnesium and aluminum alloy wheels that are made by third party manufacturers. In addition, many automobile manufacturers today limit much of their manufacturing activities to final assembly of subassemblies and other large components. For example, in the past, automobile manufacturers would purchase tires and alloy wheels from third parties, and then mount and balance the tires onto the wheels in one of their own facilities to form a TWA. Today, frequently, a third party manufacturer will purchase tires and wheels from third party suppliers, mount and balance the tires, inspect the tire wheel assemblies, and then ship the TWAs to the automobile manufacturer in a manner that allows the automobile manufacturer to minimize warehousing (just-in-time delivery). This allows the automobile manufacturer to minimize the need to warehouse TWAs at its final assembly plants, and to obtain a higher level of quality TWA that has been previously inspected and is ready to install on an automobile.

Tires and wheels are marked with certain codes under standards promulgated by various groups. These codes include information such as the name of the tire or wheel manufacturer, dimensions, wear ratings, traction ratings, dates of manufacture, etc. The Office of Vehicle Safety Compliance, under the National Highway Traffic Safety Administration (NHTSA), which is a part of the US Department of Transportation (DOT), is responsible for working with manufacturers to ensure compliance with marking requirements. The codes used in marking tires and wheels are often referred to as DOT Codes, and include information such as tire speed rating, temperature rating, tread-wear rating, manufacturer, and the like. Under Federal regulations, the TWA manufacturer is required to record the DOT Codes of all tires and wheels to be used for tracking purposes and to implement safety recalls The ability to automate the collection of DOT Codes from tires and wheels, and to determine whether a tire bead is properly seated on a wheel rim as part of the TWA assembly process, is desirable for tire manufacturers, wheel manufacturers, and TWA manufacturers. Therefore, there exists needs in the marketplace for systems and methods for automatically reading, storing, and manipulating DOT Codes from tires and wheels, and for inspecting TWAs for proper assembly, as such items are manufactured and shipped for tracking, audit, and quality control purposes.

These needs, and other needs, are addressed by one or more aspects of the present invention, although one or more aspects may not address every need.

SUMMARY OF THE INVENTION

The present invention includes many aspects and features. Moreover, while many aspects and features relate to, and are described in, the context of assembling tire wheel assemblies, the present invention is not limited to use only in this context, as will become apparent from the following summaries and detailed descriptions of aspects, features, and one or more embodiments of the present invention.

Broadly defined, various aspects in accordance with the present invention comprise a system of handling devices, imaging cameras, and computer algorithms for moving tires, wheels, and completed tire-wheel assemblies (TWAs) through a manufacturing process, and methods for efficiently training and operating such systems.

In one or more preferred implementations, a system is used to verify that a proper desired tire has been mounted on a proper desired wheel, and is further enabled to conduct various inspections on the tire and wheel. The tire inspections may be accomplished using one or more cameras that produce a three-dimensional image that is mapped into a grayscale two-dimensional image for electronic processing. The inspections may include locating the raised letters of DOT codes; reading (OCR) a tire manufacturer code (4 characters); reading (OCR) a tire type (4 characters); reading (OCR) a date of manufacture (week and year, typically 4 characters); verifying a name of the tire manufacturer; verifying a tire speed rating; verifying that the tire bead is properly seated on the wheel rim; verifying that the DOT codes are on the correct tire sidewall (top or bottom). In addition to these inspections, other inspections of the wheel may be conducted using a two-dimensional camera in grayscale. These other inspections may include verifying a center of wheel hub; and locating an outside of rim diameter. Using the data acquired in the previous two inspections, the recorded wheel image is preferably "unwrapped" for further processing, to verify correct wheel geometry and verify correct wheel color (in grayscale).

In accordance with one or more aspects, a tire height, tire width, wheel diameter, wheel offset entered into a system are utilized by a computer algorithm to calculate the expected positions required by a servo system to accomplish the centering, lifting and rotating of a TWA for 3D image processing.

In one or more preferred implementations, an additional algorithm and custom user interface fine tunes all required centering, lifting and rotating along with servo positioning of both 3D cameras to place the cameras in optimal location. This is preferably accomplished using laser distance sensing technology and servo positioning technology married with the database. In one or more preferred implementations, laser distance sensing is also used to prevent a system from accepting a TWA that is outside preset parameters, thereby protecting the system from possible damage. In one or more preferred implementations, a database of relevant data may be created by manually entering tire and wheel data, or by training the system by allowing the system to read codes from tires and wheels as they are being inspected (either in a manual training mode or automatically under certain circumstances).

Another aspect relates to a system comprising an input station configured to receive a tire wheel assembly. The system further includes a tire inspection station configured to inspect a tire of a tire wheel assembly, the tire inspection station comprising a base plate comprising an opening therein, a plurality of rollers disposed in the base plate configured to facilitate movement of a tire wheel assembly across the base plate, one or more conveyors configured to translate a tire wheel assembly across the base plate, a lifting assembly configured to lift a tire wheel assembly disposed in the tire inspection station, the lifting assembly comprising a lift jaw mechanism configured to engage a tire wheel assembly for rotative movement thereof, the lifting assembly being configured to rotate an engaged tire wheel assembly about an axis of the lifting assembly, first and second movable centering arms, the first and second movable centering arms being adjustably positionable relative to the base plate to center a hub of a tire wheel assembly relative to the lifting assembly for lifting of a tire wheel assembly, a top camera assembly disposed above the base plate, the top camera assembly including a 3D imaging camera and a laser distance sensor, and the top camera assembly being configured to translate horizontally along a first axis, and vertically along a second axis, a bottom camera assembly disposed below the base plate proximate the opening in the base plate, the bottom camera assembly including a 3D imaging camera and a laser distance sensor, and the bottom camera assembly being fixed vertically relative to the base plate but configured to translate horizontally along a third axis parallel to the first axis along an extent corresponding to the opening in the base plate. The system still further includes a wheel inspection station comprising one or more conveying assemblies configured to translate a tire wheel assembly, a dome illumination assembly comprising an opening disposed at a top thereof, a sensor configured to facilitate disposal of a tire wheel assembly under the dome illumination assembly via targeted stopping of translation of a tire wheel assembly by the one or more conveying assemblies, and a 2D camera. The system still further includes an output station, a display screen, and one or more programmable logic circuits configured to control operation of the input station, output station, tire inspection station, and wheel inspection station. The system further includes one or more non-transitory computer readable mediums collectively containing computer executable instructions for receiving a particular tire wheel assembly at the input station, translating the particular tire wheel assembly from the input station to the tire inspection station, receiving a tire wheel assembly identification number and a tire wheel assembly tracking number for the particular tire wheel assembly, retrieving, based on the tire wheel assembly identification number, first configuration parameters, positioning, based on the retrieved first configuration parameters, the first and second movable centering arms, translating, using the one or more conveyors, the particular tire wheel assembly forward over the lifting assembly, the centering arms effecting centering of the particular tire wheel assembly relative to a lifting axis of the lifting assembly, lifting, by the lifting assembly, the particular tire wheel assembly, effecting return of the first and second centering arms to a neutral position, translating the bottom camera assembly horizontally along the third axis and sampling distance measurements of the laser distance sensor of the bottom camera assembly during such translation, effecting horizontal positioning of the bottom camera assembly at a position corresponding to a minimum distance measurement read during the translation of the bottom camera assembly horizontally along the third axis, effecting vertical positioning of the particular tire wheel assembly using the lifting assembly to dispose the particular tire wheel assembly a first set off distance from the bottom imaging camera, the first set off distance being based on the first configuration parameters, translating the top camera assembly horizontally along the first axis and sampling distance measurements of the laser distance sensor of the top camera assembly during such translation, effecting horizontal positioning of the top camera assembly at a position corresponding to a minimum distance measurement read during the translation of the top camera assembly horizontally along the first axis, effecting vertical positioning of the top camera assembly to dispose the top imaging camera a second set off distance from the particular tire wheel assembly, the second set off distance being based on the first configuration parameters, engaging, by the lift jaw mechanism of the lifting assembly, the particular tire wheel assembly, rotating, by the lifting assembly, the particular tire wheel assembly four hundred degrees or more, imaging, by the top and bottom imaging cameras, top and bottom sidewalls of the particular tire wheel assembly during the rotation of the particular tire wheel assembly, rendering, based on data corresponding to the imaging by the top and bottom cameras of the top and bottom sidewalls during rotation of the particular tire wheel assembly, unwrapped images of the top and bottom sidewalls, processing the unwrapped images, such processing including locating one or more codes utilizing a pattern matching algorithm, defining three optical character recognition search regions defined relative to the located one or more codes, and reading information from the defined optical character recognition search regions, verifying that read information is on a correct tire sidewall, determining whether there is a cluster of black pixels of sufficient size that would indicate a bad bead seat, and generating one or more scores based on processing of the unwrapped images, displaying, on the display screen, the unwrapped images and a results matrix including the generated one or more scores, disengaging, by the lift jaw mechanism of the lifting assembly, the particular tire wheel assembly, lowering, by the lifting assembly, the particular tire wheel assembly to the base plate, returning the lifting assembly to a neutral position; transferring the particular tire wheel assembly from the tire inspection station to the wheel inspection station, retrieving, based on the tire wheel assembly identification number, second configuration parameters, positioning the sensor of the wheel inspection station based on the second configuration parameters, translating the particular tire wheel assembly forward using the one or more conveying assemblies of the wheel inspection station, detecting, using the sensor of the wheel inspection station, a leading edge of the particular tire wheel assembly as it is translated forward, in response to detecting the leading edge of the particular tire wheel assembly, ceasing forward translation of the particular tire wheel assembly such that it is disposed under the dome illumination assembly, imaging, by the 2D camera, the tire wheel assembly to produce a first image, locating, in the first image, a wheel center hub using a pattern matching tool, detecting, in the first image, an outside rim diameter using a circle find tool which utilizes multiple edge tools in a circular arrangement to locate the outer diameter, unwrapping, using data from locating the wheel center hub and data from detecting an outside rim diameter, an annulus region defined by such data to a rectangular region to produce a second image, comparing, using a pattern matching algorithm and the second image, specific wheel geometry of the particular tire wheel assembly to an ideal pattern, verifying, using the second image, wheel color in grayscale, and displaying, on the display screen, the first and second images and results based on the comparison of specific wheel geometry and the verification of wheel color.

In a feature of this aspect, the first set off distance and the second set off distance are the same distance.

In a feature of this aspect, the system comprises one programmable logic circuit for each station.

In a feature of this aspect, the system comprises a single programmable logic circuit configured to operate all of the stations.

In a feature of this aspect, the system comprises a plurality of programmable logic circuits.

In a feature of this aspect, the system further comprises an input device.

In a feature of this aspect, the system comprises a plurality of servos.

In a feature of this aspect, the lift jaw mechanism is configured to provide sufficient force so no slippage occurs during rotation of an engaged tire wheel assembly.

In a feature of this aspect, the system further comprises one or more indicator lights.

In a feature of this aspect, the system comprises greed and red indicator lights.

In a feature of this aspect, the first set off distance and the second set off distance are different distances.

Another aspect relates to a system comprising an input station configured to receive a tire wheel assembly. The system further includes a tire inspection station configured to inspect a tire of a tire wheel assembly, the tire inspection station comprising a base plate comprising an opening therein, a plurality of rollers disposed in the base plate configured to facilitate movement of a tire wheel assembly across the base plate, one or more conveyors configured to translate a tire wheel assembly across the base plate, a lifting assembly configured to lift a tire wheel assembly disposed in the tire inspection station, the lifting assembly comprising a lift jaw mechanism configured to engage a tire wheel assembly for rotative movement thereof, the lifting assembly being configured to rotate an engaged tire wheel assembly about an axis of the lifting assembly, first and second movable centering arms, the first and second movable centering arms being adjustably positionable relative to the base plate to center a hub of a tire wheel assembly relative to the lifting assembly for lifting of a tire wheel assembly, a top camera assembly disposed above the base plate, the top camera assembly including a 3D imaging camera and a laser distance sensor, and the top camera assembly being configured to translate horizontally along a first axis, and vertically along a second axis, a bottom camera assembly disposed below the base plate proximate the opening in the base plate, the bottom camera assembly including a 3D imaging camera and a laser distance sensor, and the bottom camera assembly being fixed vertically relative to the base plate but configured to translate horizontally along a third axis parallel to the first axis along an extent corresponding to the opening in the base plate. The system still further includes a wheel inspection station comprising one or more conveying assemblies configured to translate a tire wheel assembly, a dome illumination assembly comprising an opening disposed at a top thereof, a sensor configured to facilitate disposal of a tire wheel assembly under the dome illumination assembly via targeted stopping of translation of a tire wheel assembly by the one or more conveying assemblies, and a 2D camera. The system still further includes an output station, a display screen, and one or more programmable logic circuits configured to control operation of the input station, output station, tire inspection station, and wheel inspection station.

Another aspect relates to a method comprising receiving a particular tire wheel assembly at an input station, translating the particular tire wheel assembly from the input station to a tire inspection station, receiving a tire wheel assembly identification number and a tire wheel assembly tracking number for the particular tire wheel assembly, retrieving, based on the tire wheel assembly identification number, first configuration parameters, positioning, based on the retrieved first configuration parameters, first and second movable centering arms, translating, using one or more conveyors, the particular tire wheel assembly forward over a lifting assembly, the centering arms effecting centering of the particular tire wheel assembly relative to a lifting axis of the lifting assembly, lifting, by the lifting assembly, the particular tire wheel assembly, effecting return of the first and second centering arms to a neutral position, translating a bottom camera assembly horizontally and sampling distance measurements of a laser distance sensor of the bottom camera assembly during such translation, effecting horizontal positioning of the bottom camera assembly at a position corresponding to a minimum distance measurement read during the translation of the bottom camera assembly horizontally, effecting vertical positioning of the particular tire wheel assembly using the lifting assembly to dispose the particular tire wheel assembly a first set off distance from a bottom imaging camera of the bottom camera assembly, the first set off distance being based on the first configuration parameters, translating a top camera assembly horizontally and sampling distance measurements of a laser distance sensor of the top camera assembly during such translation, effecting horizontal positioning of the top camera assembly at a position corresponding to a minimum distance measurement read during the translation of the top camera assembly horizontally, effecting vertical positioning of the top camera assembly to dispose a top imaging camera of the top camera assembly a second set off distance from the particular tire wheel assembly, the second set off distance being based on the first configuration parameters, engaging, by a lift jaw mechanism of the lifting assembly, the particular tire wheel assembly, rotating, by the lifting assembly, the particular tire wheel assembly four hundred degrees or more, imaging, by the top and bottom imaging cameras, top and bottom sidewalls of the particular tire wheel assembly during the rotation of the particular tire wheel assembly, rendering, based on data corresponding to the imaging by the top and bottom cameras of the top and bottom sidewalls during rotation of the particular tire wheel assembly, unwrapped images of the top and bottom sidewalls, processing the unwrapped images, such processing including locating one or more codes utilizing a pattern matching algorithm, defining three optical character recognition search regions defined relative to the located one or more codes, and reading information from the defined optical character recognition search regions, verifying that read information is on a correct tire sidewall, determining whether there is a cluster of black pixels of sufficient size that would indicate a bad bead seat, and generating one or more scores based on processing of the unwrapped images, displaying, on a display screen, the unwrapped images and a results matrix including the generated one or more scores, disengaging, by the lift jaw mechanism of the lifting assembly, the particular tire wheel assembly, lowering, by the lifting assembly, the particular tire wheel assembly to a base plate, returning the lifting assembly to a neutral position below the base plate; translating the particular tire wheel assembly from the tire inspection station to a wheel inspection station, retrieving, based on the tire wheel assembly identification number, second configuration parameters, positioning a sensor of the wheel inspection station based on the second configuration parameters, translating the particular tire wheel assembly forward using one or more conveying assemblies of the wheel inspection station, detecting, using the sensor of the wheel inspection station, a leading edge of the particular tire wheel assembly as it is translated forward, in response to detecting the leading edge of the particular tire wheel assembly, ceasing forward translation of the particular tire wheel assembly such that it is disposed under a dome illumination assembly, imaging, by a camera, the tire wheel assembly to produce a first image, locating, in the first image, a wheel center hub using a pattern matching tool, detecting, in the first image, an outside rim diameter using a circle find tool which utilizes multiple edge tools in a circular arrangement to locate the outer diameter, unwrapping, using data from locating the wheel center hub and data from detecting an outside rim diameter, an annulus region defined by such data to a rectangular region to produce a second image, comparing, using a pattern matching algorithm and the second image, specific wheel geometry of the particular tire wheel assembly to an ideal pattern, verifying, using the second image, wheel color in grayscale, and displaying, on the display screen, the first and second images and results based on the comparison of specific wheel geometry and the verification of wheel color.

Another aspect relates to a tire-wheel assembly (TWA) inspection system that allows for automatic inspection of tire type, wheel type, data capture of all relevant DOT codes, and other information that is necessary or desirable for tracking and auditing tires, wheels, and TWAs through the supply chain. The TWA inspection system also allows for easy audit of all captured information for quality control and safety recall purposes.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

Additionally, further areas of applicability of the present invention will become apparent from the detailed description provided hereinafter. It should be understood that the detailed description and specific examples, while indicating one or more preferred embodiments, are intended for purposes of illustration only and are not intended to limit the scope of the invention.

BRIEF DESCRIPTION OF THE DRAWINGS

One or more preferred embodiments of the present invention now will be described in detail with reference to the accompanying drawings, wherein the same elements are referred to with the same reference numerals, and wherein.

DETAILED DESCRIPTION

Figure 1:
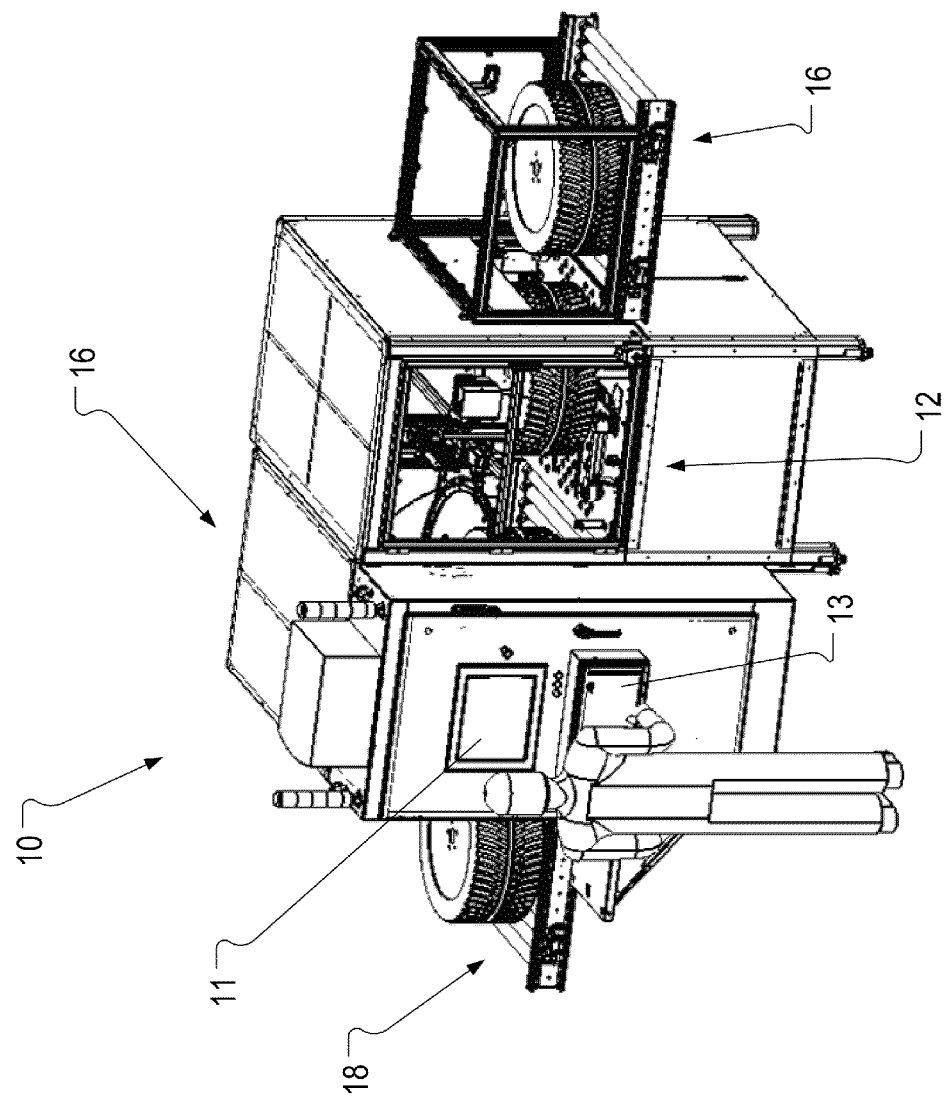
FIG. 1 illustrates an exemplary system in accordance with one or more preferred implementations which includes a tire inspection station, a wheel inspection station, an input station, and an output station.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. §112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

FIG. 1 illustrates an exemplary system 10 in accordance with one or more preferred implementations which includes a tire inspection station 12, a wheel inspection station 14, an input station 16, and an output station 18.

In some preferred implementations, each station uses a programmable logic controller (PLC) or other controller to control the movements of inspection apparatus including cameras and servos, while in some preferred implementations, a single PLC or other controller controls all stations.

In a preferred implementation, the system 10 uses a separate software application at some or all of each of the four stations to complete the inspection process. In one or more preferred implementations, a system includes a tire inspection application or module which controls a tire inspection process, a wheel inspection application or module which controls a wheel inspection process, a user interface application or module which controls a user interface to one or more PLCs or other controllers, and a database or database application.

In one or more preferred implementations, the system 10 includes one or more displays devices and input devices associated therewith, such as display device 11 and input device 13 illustrated in FIG. 1.

While one or more preferred implementations use a single PLC or other controller, it is understood that multiple PLCs or other means may be used as needs dictate. Each of the applications may communicate with one or more of the other applications using one or more PLCs as a central point of communication, or the applications may communicate with each other over a network.

Figure 2A:
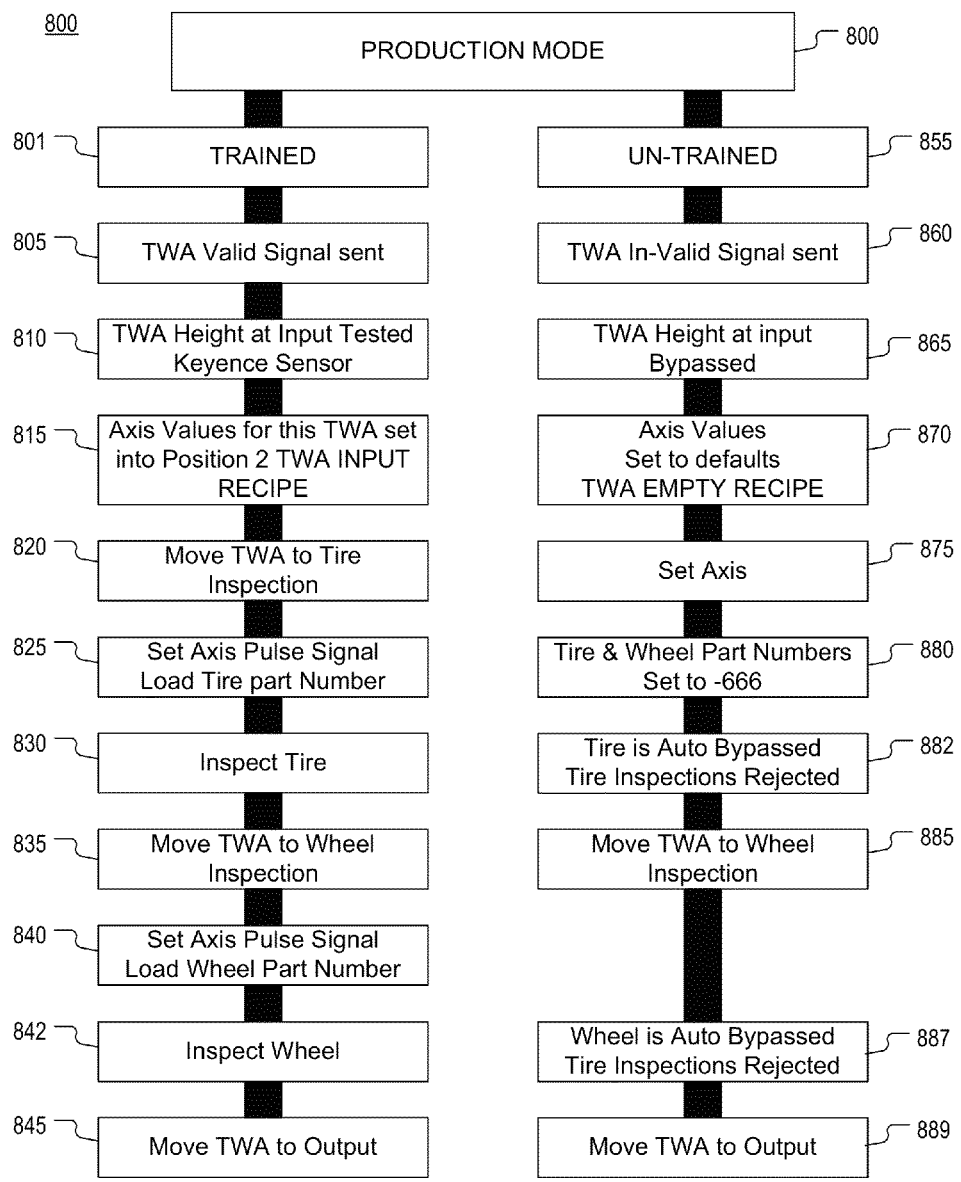
FIG. 2A illustrates a flowchart for an exemplary process for inspecting a tire and wheel assembly (TWA) using the system of FIG. 1.

FIG. 2A illustrates a flowchart for an exemplary process 800 for inspecting a tire and wheel assembly (TWA) using the system 10.

The exemplary TWA inspection process 800 begins when a tire and wheel assembly is conveyed to the input station 16 of the system.

This can be accomplished manually or using a conveying system or other apparatus facilitating transfer of a TWA to the input station 16. Preferably, a TWA remains in a queue until the system verifies a TWA identification number (from the conveying system or by other means if no conveyor is present) and records a TWA tracking number used by the TWA manufacturer. The TWA identification number is used to find previously stored inspection parameters associated with a given tire-wheel combination, and the TWA tracking number is used to physically track each TWA in the manufacturing process as it is conveyed through the TWA manufacturing and inspection processes. Preferably, a broadcast system comprising part of the system or another system communicates with the system to deliver the TWA identification number and the tracking number. Before proceeding, the system determines whether a TWA is "valid", "invalid", or "untrained".

If the TWA tracking number is not associated with a valid TWA identification number or is otherwise not found in the database, the process proceeds to step 855. At step 855, the TWA is determined to be either "untrained" or "invalid". If the TWA identification number is found but no data is associated with the TWA identification number, the TWA is determined to be "untrained". If the TWA identification number is not found, the TWA is determined to be "invalid", a code is entered into the broadcast system and associated with the TWA tracking number, all of the system servos are retracted to safe positions and the TWA is automatically pushed through the remaining stations un-inspected and is identified by tracking number as being rejected.

If the TWA is categorized as untrained (e.g. data is unavailable, but the TWA falls within acceptable physical dimensions), it is automatically pushed through the remaining stations un-inspected and is identified as rejected, but may be inspected later once the proper parameters are added to the system. The system preferably continuously checks to make sure only valid TWAs are inspected and protects the system against unknown or unwanted TWAs. In order to add a new set of data for a specific tire-wheel combination, the system may be used in a training mode to capture the relevant data and store it in the database under a new TWA identification number.

If the input station determines that a TWA is "untrained", the process proceeds to step 865 where the TWA height input is bypassed. Proceeding to step 870, default axis values are entered into the system, and the default axis positions are set at step 875. At step 880, the tire and wheel part numbers are set to a default value, the process proceeds to step 882 where the tire inspection process is terminated, and the TWA is moved to a wheel inspection station at step 885. At step 887, the wheel inspection process is terminated, and the TWA is moved to an output station at step 889, where the TWA tracking number is updated to indicate that manual training is required in order to inspect the TWA, and the process ends.

Referring back to step 800, if the TWA identification number is found and relevant inspection data is available, the process proceeds to step 801 where the system loads relevant data associated with the TWA under inspection from a database containing data for a plurality of tires and wheels which can be used in tire-wheel combinations, and/or for various tire-wheel combinations.

Proceeding to step 805, a "valid" signal is sent to the tire inspection station, and the process proceeds to step 810 where a first laser distance sensor measures the tire height to determine if it is within an acceptable range for the TWA inspection system. If the TWA is valid, and the tire height is measured to be within range of the laser distance sensor, it enters the system 10. Proceeding to step 815, axis data for a plurality of components of the system 10 is loaded for the detected TWA from a database. The input station uses the data loaded from the database to set a plurality of servo positioning axes to properly locate each servo position for inspection.

Proceeding to step 820, the process then continues as the TWA enters a tire inspection station, and the data from the input station 16 is transferred to the tire inspection station 12. At step 825, the process locates and loads the proper tire inspection program based on the TWA identification number and sends the data to the tire inspection station 12, and the axis positions are loaded into the tire inspection station 12 that are then used to center, lift and rotate the TWA for a 3D camera inspection. All the axis positions are now loaded from the tire inspection recipe to the required axes for this particular TWA.

Figure 2B:
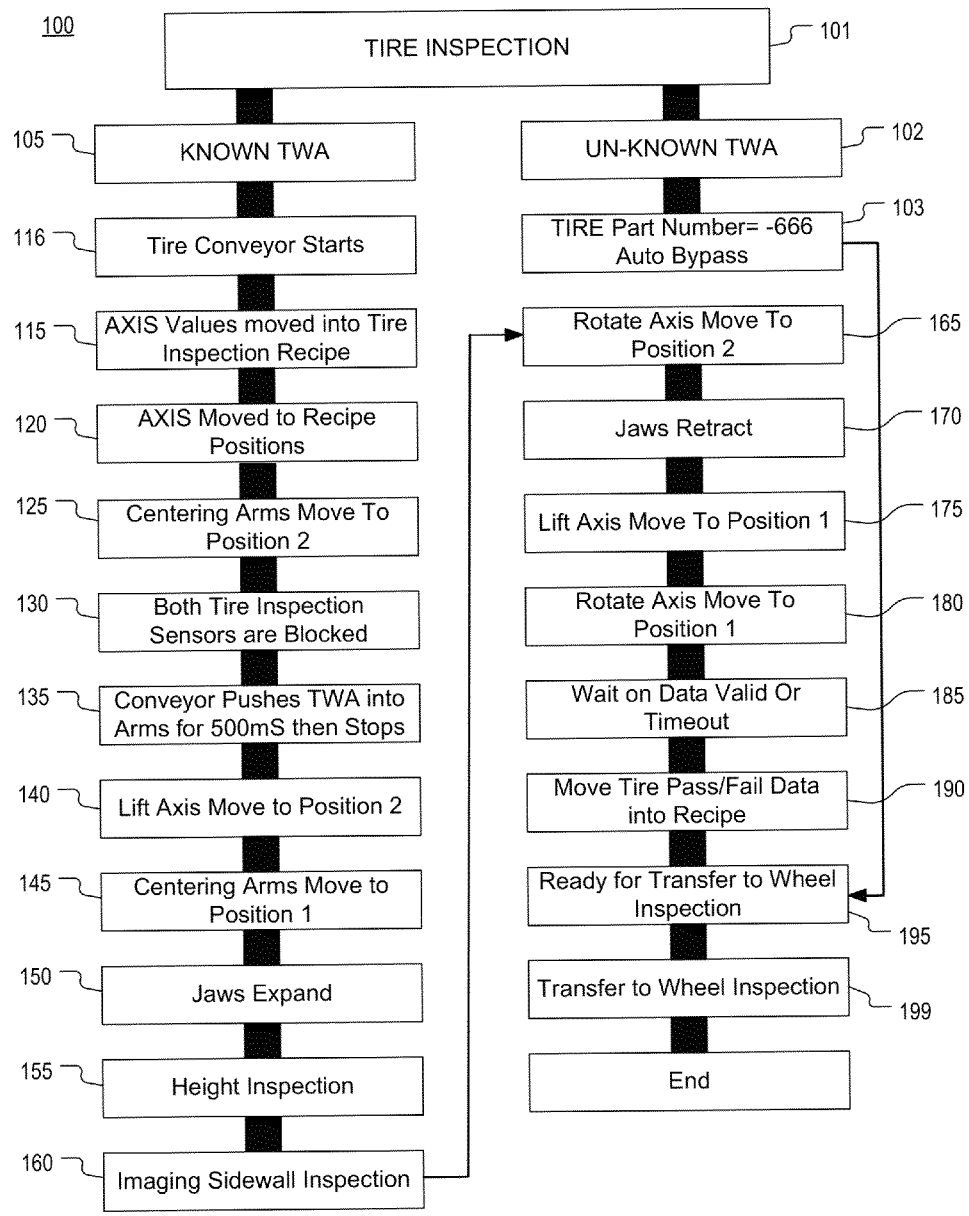
FIG. 2B illustrates a flowchart for an exemplary process for inspecting a tire utilizing the tire inspection station of the system of FIG. 1.

At step 830, a tire inspection process, such as the tire inspection process 100 illustrated in FIG. 2B, commences and the tire of the TWA is inspected. The results of the inspection are recorded by the system, and the process proceeds to step 835, where the TWA is passed to a wheel inspection station.

At step 840, the relevant wheel inspection data associated with the TWA identification number is loaded into the wheel inspection station. At step 842, the wheel of the TWA is inspected. At step 845, the wheel inspection is completed, the data associated with the TWA tracking number is updated, and the TWA moves to an output station.

Looking at the tire inspection process more closely, FIG. 2B illustrates a flowchart for an exemplary process 100 for inspecting a tire utilizing the tire inspection station 12. The system comprises apparatus for centering a tire wheel assembly in the tire inspection station 12.

Figure 3:
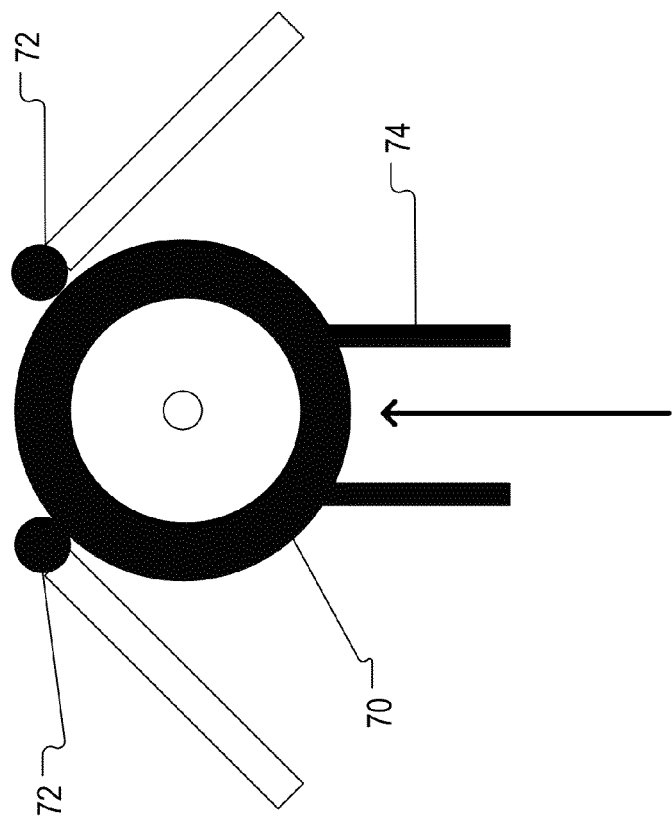
FIG. 3 is a schematic illustration of apparatus for centering a tire wheel assembly in a tire inspection station.

FIG. 3 schematically illustrates exemplary such apparatus. Specifically, FIG. 3 illustrates an exemplary TWA 70 that is driven forward, e.g. by tire conveyor chains 74. Two centering arms are extended to a pre-programmed position (based the stored dimensions of a known TWA as determined by means such as a TWA identification number as described hereinbelow), and the tire conveyor chains 74 push the TWA against the centering arms 72, preferably resulting in a hub of the TWA being centered over a lifting assembly.

These centering arms 72 are positioned and configured to center such TWA relative to the lifting assembly. The lifting assembly is configured to lift the TWA vertically and cause the lift jaws to engage the TWA 70 and rotate it.

In one or more preferred implementations, the centering arms 72 can be adjusted inward or outward to adjust positioning of a TWA, to ensure centering of a received TWA relative to the lift jaws.

Preferably, the centering arms 72 are servo controlled and are utilized to achieve accurate and repeatable TWA positioning so the lift assembly can operate reliably and repeatedly. Preferably, one or more dedicated databases storing data for a plurality of TWAs and the repeatability and accuracy of the servo control enable consistent TWA centering.

Figure 4:
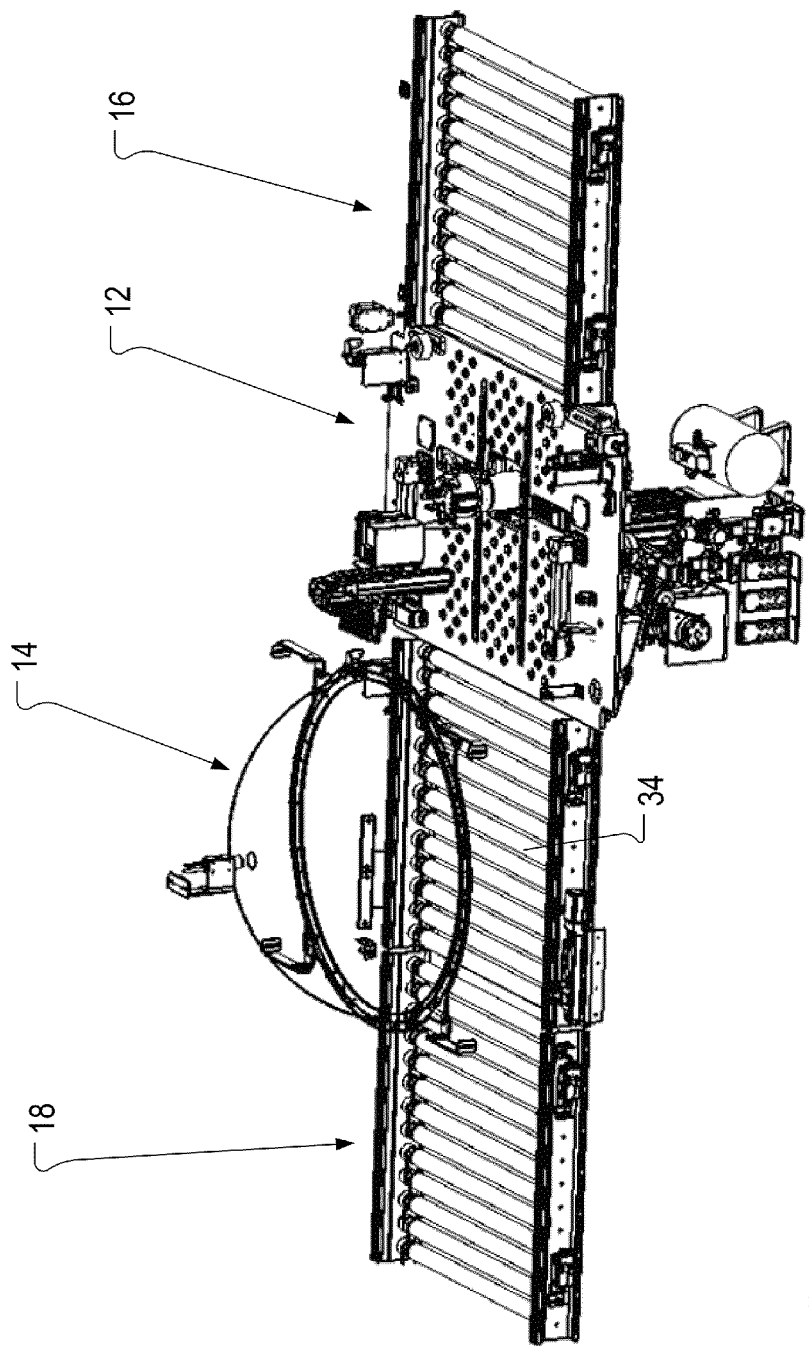
FIGS. 4-9 illustrates the system of FIG. 1, with various components omitted from each of the views.
Figure 5:
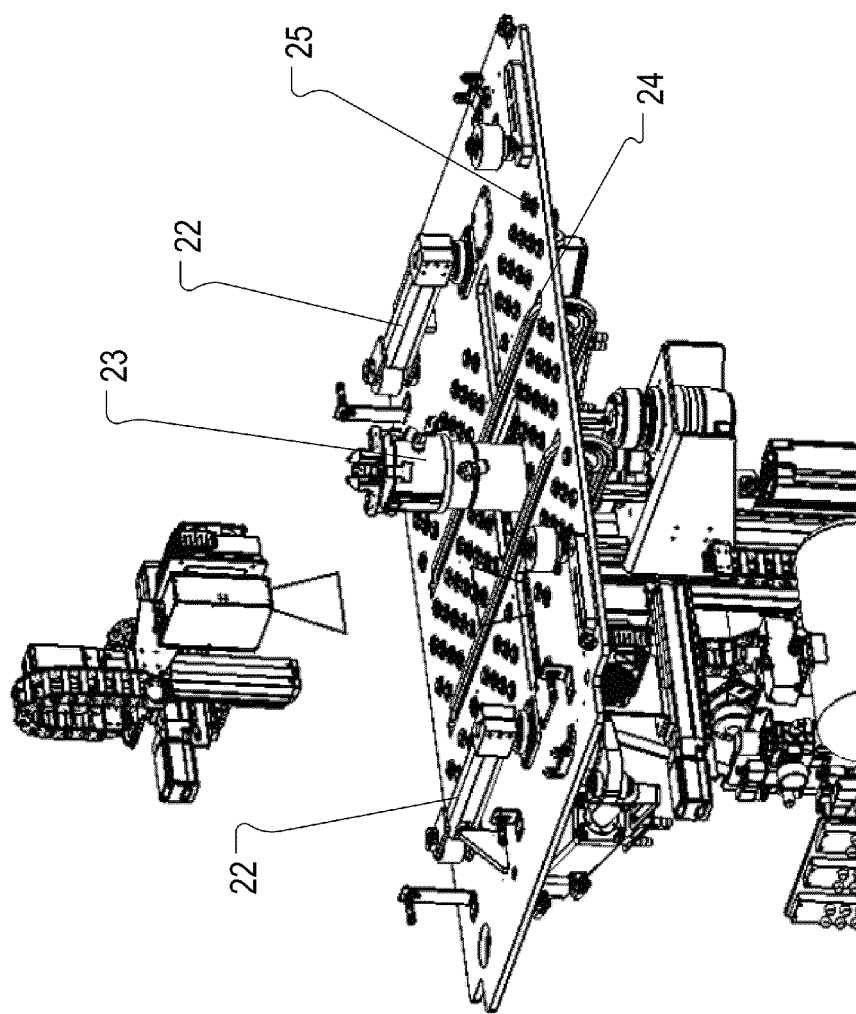
Figure 6:
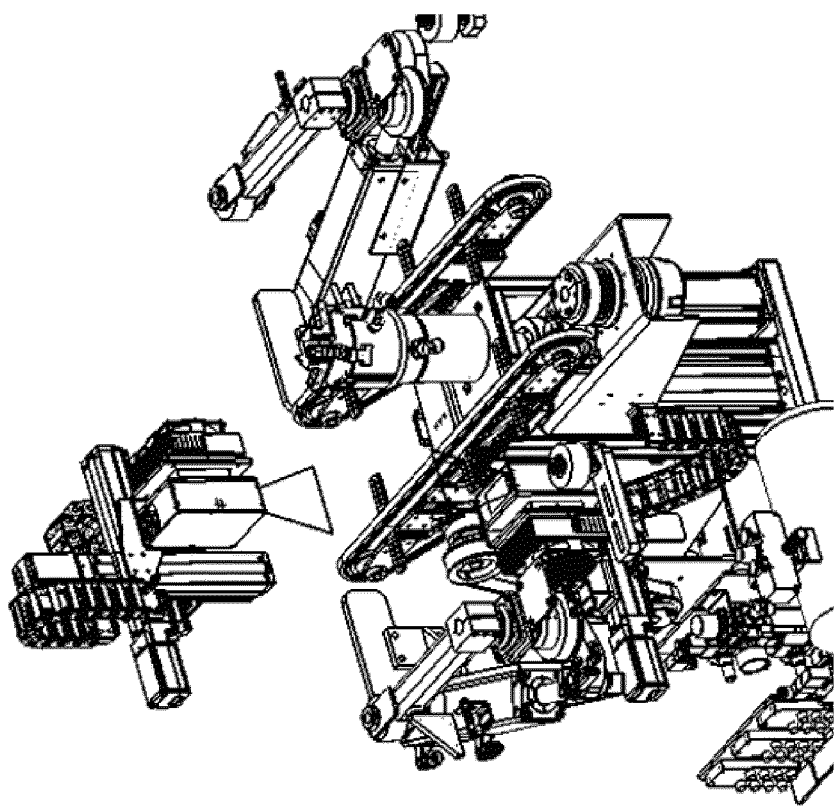
Figure 7:
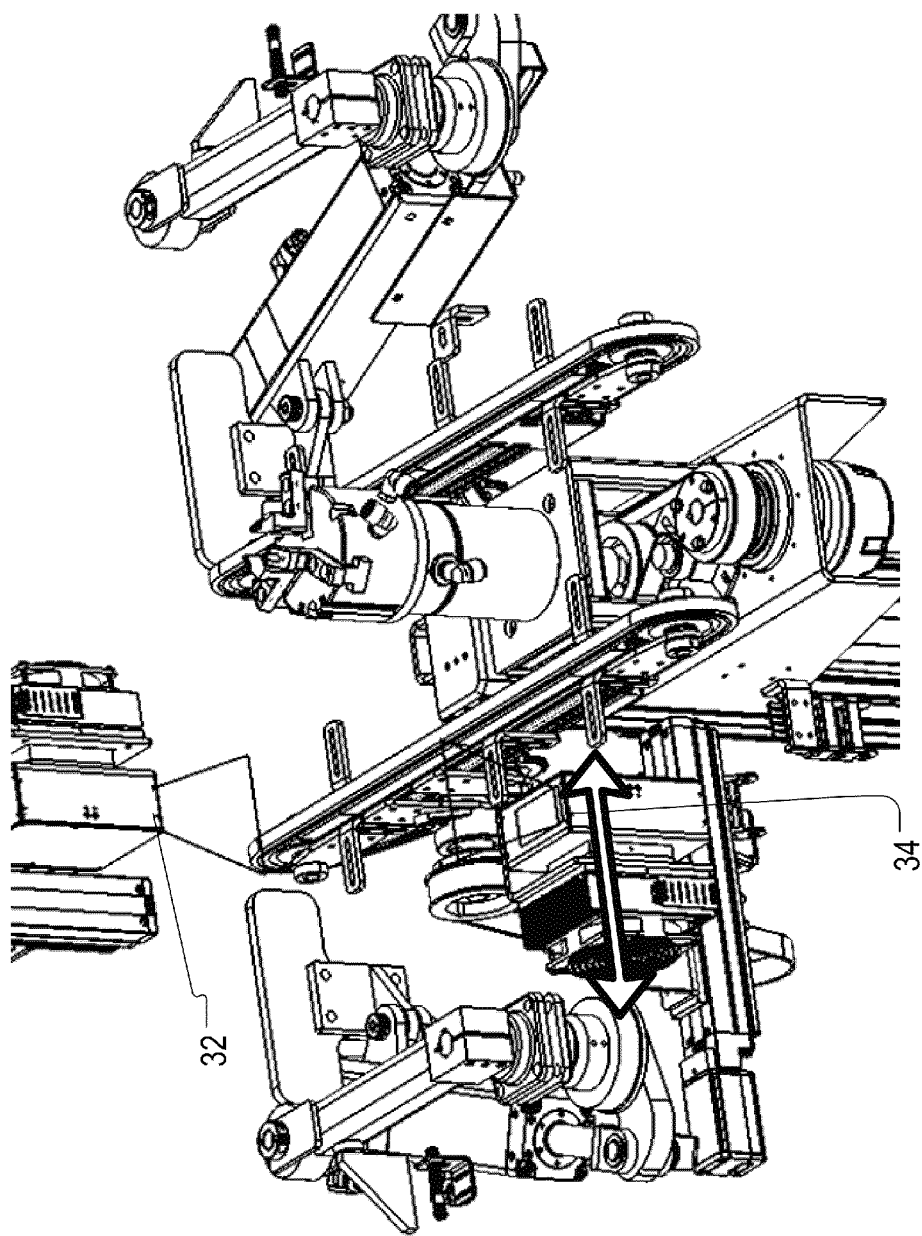

Returning to the system 10 of FIG. 1, the system 10 includes such apparatus for centering a TWA. FIG. 4 illustrates the system 10 of FIG. 1, with some components omitted from the illustration to better illustrate such apparatus, and FIG. 5 illustrates a still closer view with still more components omitted. FIG. 6 is similar to FIG. 5, but further omits illustration of a base plate for illustratative purposes. FIG. 7 is similar to FIG. 6, but omits illustration of still more components.

Specifically, as perhaps best seen in FIG. 5, the system 10 includes centering arms 22 serving the same function as the centering arms 72 of FIG. 3. Just like the centering arms 72, the centering arms 22 are adjustable to adjust centering of a TWA disposed in the tire inspection station 12 relative to lifting assembly 23, which is configured to engage, lift, and rotate such a centered TWA.

The lifting assembly 23 is illustrated in an extended configuration in FIG. 5, but is configured to ascend and descend, and can descend from the extended configuration illustrated in FIG. 5 to a retracted configuration.

In a preferred methodology of use, when the lifting assembly 23 is in a retracted configuration, a TWA entering the tire inspection station 12 is driven forward by tire conveyors 24. Movement of a TWA across a base plate of the inspection station 12 is facilitated by rollers 25 disposed in the base plate. The centering arms 72 center the TWA, and the lifting assembly 23 engages the TWA and ascends to an extended configuration, thereby lifting the TWA for rotation of the TWA.

With reference to FIG. 2, an exemplary tire inspection process 100 begins at step 101, where the system 10 determines if a TWA identification number is known to the system. Based on this determination, the process proceeds to either step 102 or step 110.

Down one of these paths, if a TWA identification number cannot be identified or the TWA identification number is not known, the process proceeds to step 102 to acknowledge the unknown number, and proceeds to step 103 where the TWA identification number is logged as unavailable, e.g. via use of a dummy identification number. The tire inspection process is then basically "skipped", and the process proceeds to step 195, where the TWA is ready for transfer to a wheel inspection station, and then proceeds to step 199 where the TWA is transferred to the wheel inspection station and the process 100 ends.

Returning to step 101, on the alternate branch, if the TWA identification number is known to the system, the relevant inspection data is loaded into the system and the process proceeds to step 110, where a conveyor or other means starts and moves the TWA to the tire inspection station.

At step 115, the system pulls relevant axis positions for various components of the system (including, for example, cameras, sensors, and servos) from a database and loads the same into the inspection station, and at step 120 the system adjusts the various sensors and cameras to allow the tire inspection steps to commence. At step 125, the centering arms 22 move to a pre-programmed position that corresponds to the size of the identified incoming TWA, thereby preparing the system to facilitate centering of an incoming TWA in the inspection station relative to the center of the wheel hub at step 135.

At step 130, tire inspection sensors are blocked by the tire, which indicates to the system that a TWA is in position and ready to be inspected. At step 135, the conveyors 24 push the TWA into the centering arms and then stop, thereby centering the TWA in preparation for tire inspection. At step 140, the lift assembly adjusts to a programmed height that corresponds to the size of the identified incoming TWA, thereby preparing the system to ensure that the incoming TWA in the inspection station will be in the proper vertical position in the following steps.

Once TWA centering has been accomplished, the centering arms are retracted to a neutral position at step 145 so that they do not interfere with wheel clamping. At step 150, wheel clamping jaws of the lift assembly are extended to clamp the TWA for controlled rotation of the TWA. The TWA is then lifted to a proper height and clamping jaws of the lifting assembly are extended to completely center the wheel on the lift/rotate axis. The jaws are designed to center the wheel on a rotation axis of the lifting assembly and provide enough clamping force so no slippage occurs during TWA rotation. This facilitates rotation of the TWA about the rotation axis of the lifting assembly.

The system 10 further includes a top imaging camera 32 and a bottom imaging camera 34, as can be seen in FIG. 7. A schematic field of imaging (which may or may not correspond to the actual field of imaging for such an imaging camera) for each of these imaging cameras 32,34 is illustrated in FIG. 7 as well.

Figure 8:
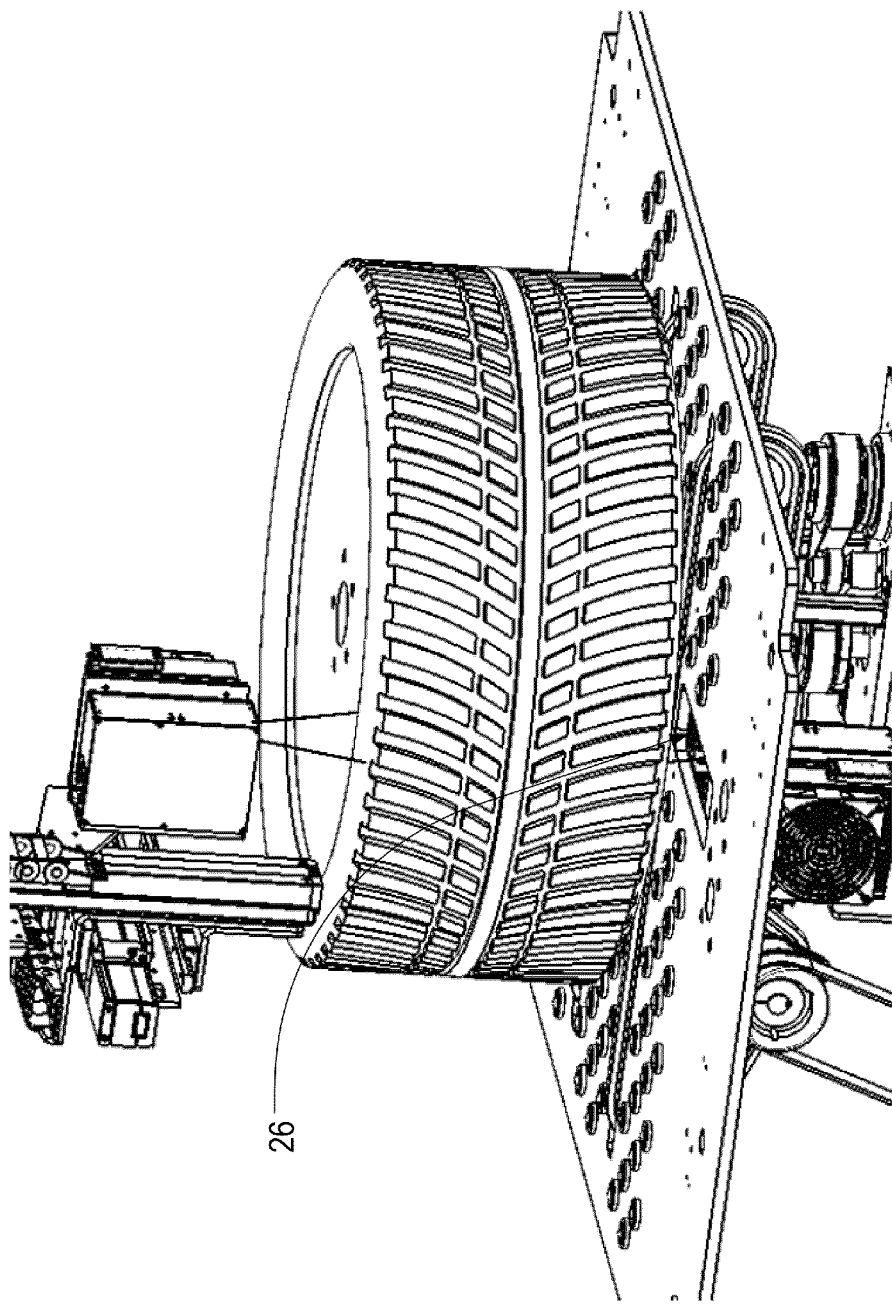
Figure 9:
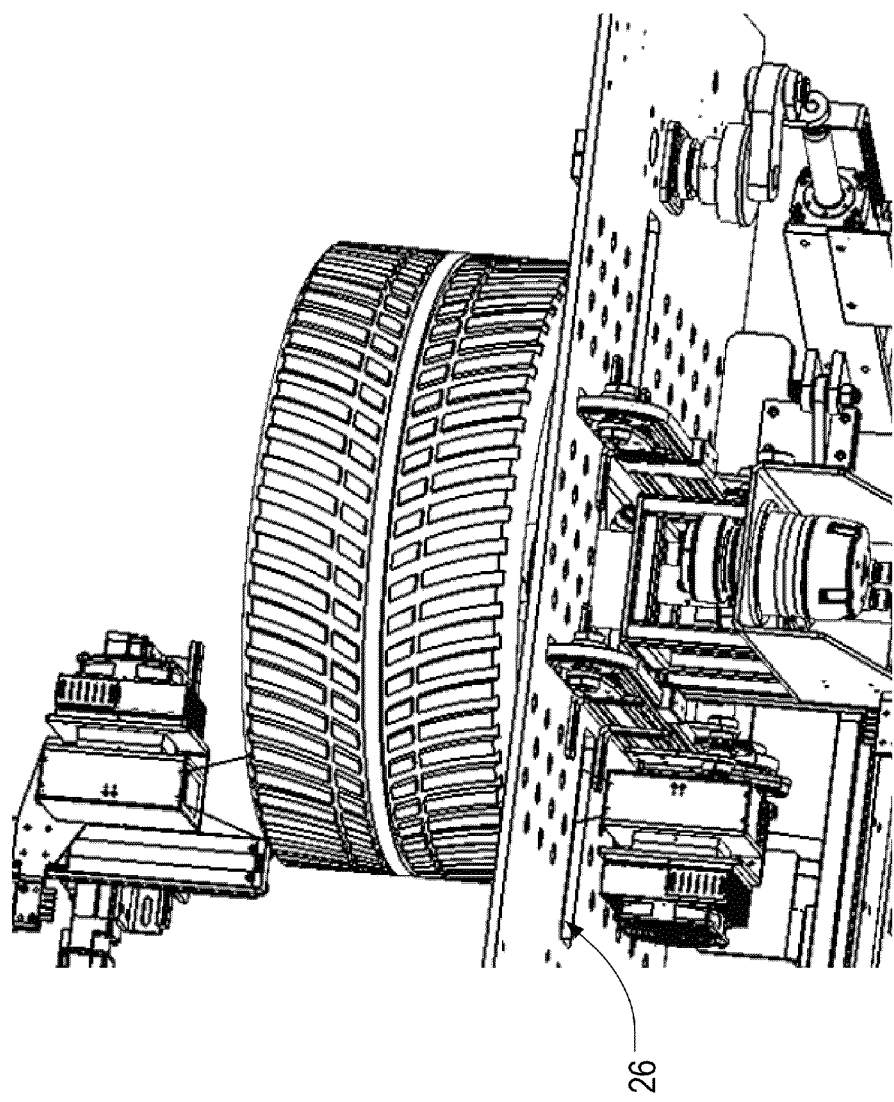

These imaging cameras 32,34 can image sidewalls of a TWA that has been lifted by the lifting assembly 23, as illustrated in FIGS. 8 and 9. As illustrated in these figures, an opening 26 in the base plate of the inspection station 12 allows the bottom imaging camera 34 to image the TWA.

In one or more preferred implementations, automatic servo positioning of tire presentation axes is accomplished by an algorithm developed to consistently place the imaging cameras 32,34 in a repeatable position so as to enhance the tire sidewall inspection process. In a preferred implementation, the automatic positioning uses laser distance sensors in concert with servo driven motion control to accomplish this.

At step 155, tire height inspection commences whereby the system determines the peak height of both the inner and outer tire sidewalls, which such information is in turn used to position an imaging camera in reference to each of the inner and outer tire sidewalls.

Specifically, in one or more preferred implementations, the system 10 is configured to tune the distance between the imaging cameras 32,34 and a TWA lifted by the lifting assembly 23.

In an exemplary methodology, first, the lifting assembly 23 raises the TWA to an "expected" position. Preferably, this position is derived from data entered into a database that includes tire width, tire height, wheel diameter, and wheel offset. Once the lift is at the expected position, an automatic positioning sequence can take over.

Preferably, each of the imaging cameras 32,34 includes, functions as, or is disposed adjacent a laser distance sensor.

The bottom imaging camera 34 and laser distance sensor is preferably configured to adjust horizontally as illustrated by the double sided arrow in FIG. 7. In a preferred methodology, the laser distance sensor is moved to a "zero" position, e.g. to the far left with respect to FIG. 7, and then a servo effects movement of the bottom laser distance sensor horizontally to the right while sampling distances (e.g. vertically) from the bottom laser distance sensor. After motion is complete, the minimum distance position that was sampled is determined. This corresponds to the "high point" of the tire sidewall.

Figure 10A:
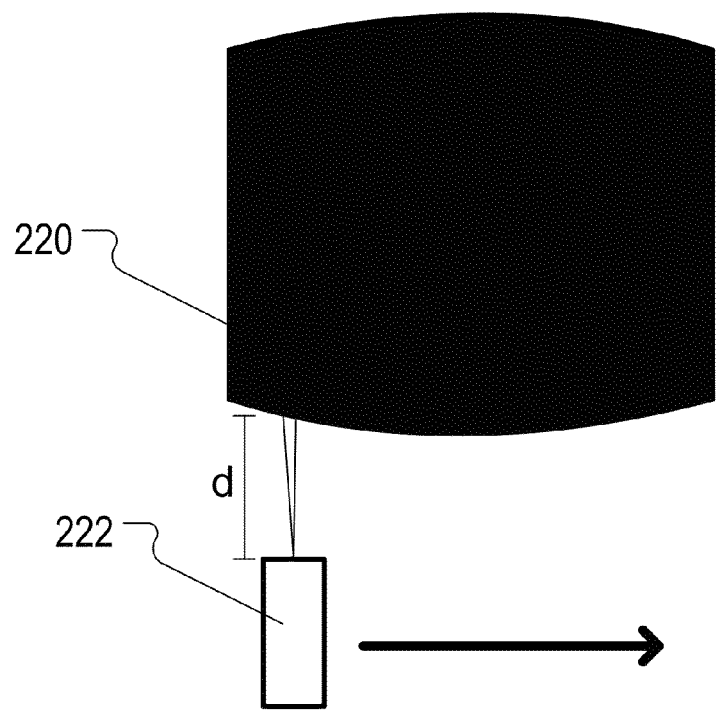
FIGS. 10A-D schematically illustrates a process for determining the high point of a tire sidewall.
Figure 10B:
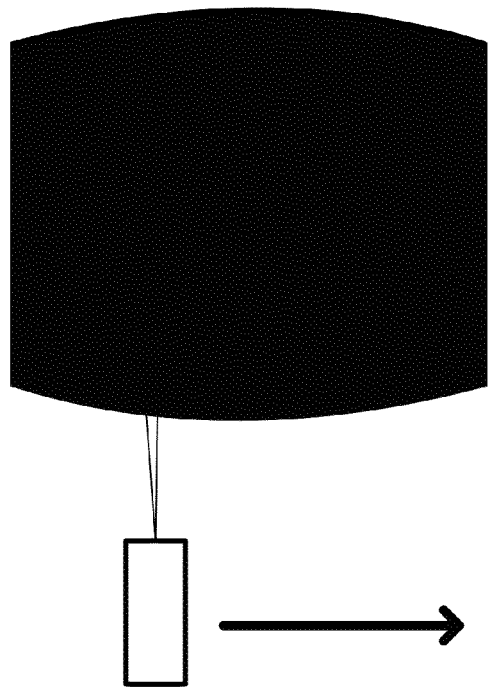
Figure 10C:
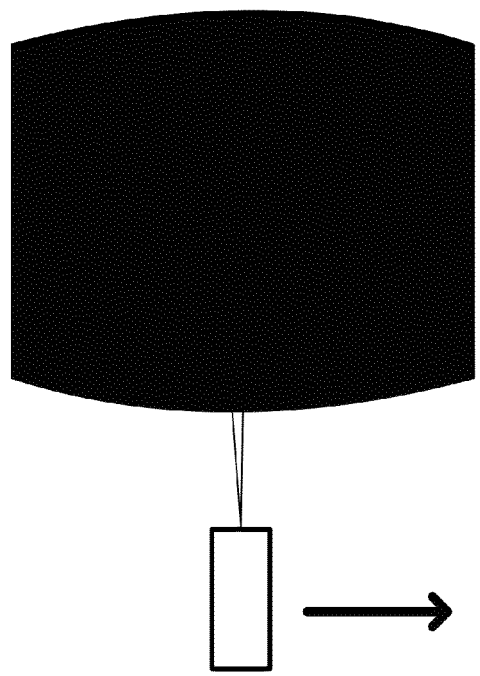
Figure 10D:
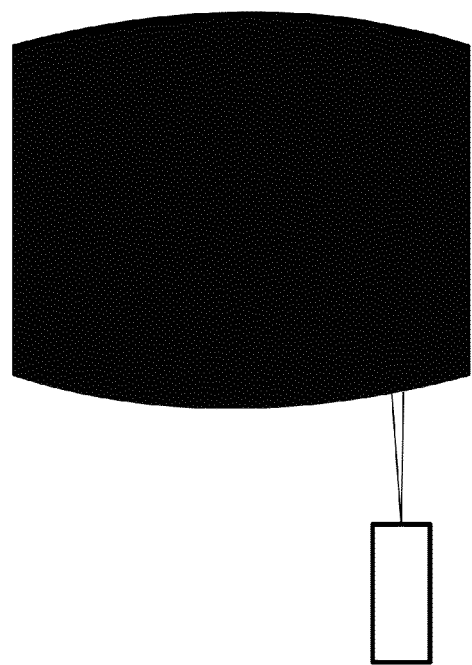

This process is schematically illustrated in FIGS. 10A-D. These figures schematically illustrate a portion of a tire 220 and a laser distance sensor 222 that travels horizontally from an initial position in FIG. 10A to a final position while sampling a vertical distance d from the laser distance sensor 222 to the tire 220 as it travels. The distance d sampled in FIG. 10C is determined to be the minimum distance, which indicates that this "x" position corresponds to the "high point" of the sidewall of the tire 220.

Returning to the system 10, the system uses the horizontal position the bottom laser distance sensor was at when the minimum vertical distance was sampled as the "x" axis position of the laser imaging camera, and the servo positions the bottom imaging camera 34 at this position. In one or more preferred implementations, this is accomplished by again sampling while moving the bottom laser distance sensor until it reads the minimum value.

Next, based on a measurement from the bottom laser distance sensor, the lifting assembly is adjusted to cause the distance between the bottom laser imaging camera 34 and the tire to be a desired standoff distance, such as seventy millimeters.

In such a methodology of use, the proper standoff distance has preferably already been determined, and is loaded from a database. Preferably, the database includes preferred standoff distances for a plurality of TWAs or TWA makes/types.

In one or more preferred implementations, to determine the proper standoff distance, the TWA lift axis servo positions are calibrated and taught by a technician utilizing an expected position algorithm and a fine position tuning algorithm. The distances may be determined during manual training (a user manually moves the lift axis to the desired position and records the distance in a database) or automatically (the system may use an iterative process to determine the best distance by trial and error when an unknown TWA is encountered by the system). The bottom laser distance sensor verifies the correct standoff distance and also is used to do a fine measurement on the tire height. Preferably, during use of the system, a tire height of a tire of a TWA must meet a narrow tolerance to verify it is the correct tire for the TWA (i.e.; a front tire vs. a rear tire or vice versa). A front tire and a rear tire of a "matched set" may only differ in height by 1" or less.

A process similar to that described with respect to the bottom laser distance sensor is utilized with the top laser distance sensor to determine a center of a top sidewall of the tire of the TWA being inspected, and the top imaging camera 32 is then positioned along an "x" axis based thereon.

Figure 11:
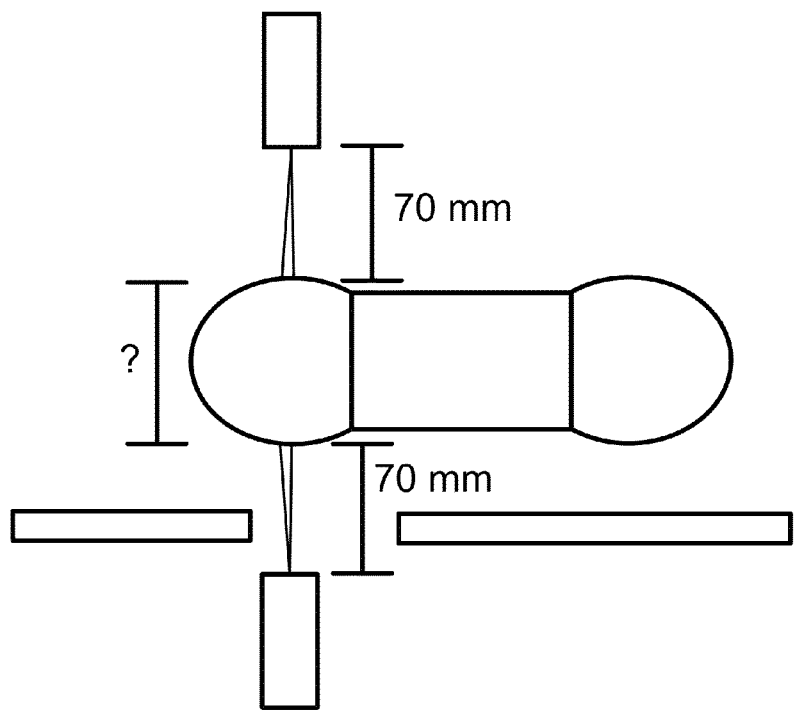
FIG. 11 schematically illustrates top and bottom standoff distances for top and bottom imaging cameras.

Preferably, unlike the bottom imaging camera 34, the top imaging camera 32 is translatable up and down. Preferably, the top imaging camera is adjusted vertically to position the top imaging camera 32 at a desired standoff from the tire, such as seventy millimeters. Preferably, the desired standoff distance for the top imaging camera and the desired standoff distance for the bottom imaging camera are the same, as illustrated schematically in FIG. 11.

Consistent camera positioning and repeatable and accurate results are facilitated by the interconnection between a TWA database and accurate and repeatable servo positioning.

With all axes in the proper positions, both the top and bottom laser distance sensors acquire the tire top and tire bottom positions. The tire height is calculated and an allowed variance is checked to verify that it falls within a range of acceptable tire heights stored in the database. Preferably, a PLC or other controller uses a database and servo positioning to ensure that the inspection process is robust and repeatable.

A trigger signal is sent from the PLC or other controller to initiate the tire inspection process, and at step 160, the tire sidewall imaging process begins as the top and bottom imaging cameras 32,34 commence to scan and record an image of the inner and outer sidewalls. Preferably, at step 165, the TWA is rotated about the rotation axis of the lifting assembly in at least a complete rotation, and preferably more than a complete rotation, such as four hundred and twenty degrees, to allow an overlapping image of each sidewall to be recorded.

The imaging process begins by starting a rotation of the TWA about the rotation axis and starting encoder clocks for processing. Preferably, an encoder is mounted directly to the shaft of the lifting assembly that provides the TWA rotation. This allows both the top and bottom imaging cameras 32,34 to acquire consistent and repeatable images even though the velocity and acceleration of the rotation may change. The overall rotation is preferably greater than three hundred and sixty degrees in order to ensure that image "overlap" occurs to get a complete image of all the features required for the inspection process. In one or more preferred implementations, the imaging cameras are triggered from the PLC when the TWA starts rotating, the imaging cameras 32,34 acquire all the profile data of four hundred degrees of rotation and then converts such data into an 8 bit grayscale image. Once the image is built, it is preferably passed one or more vision application tools for processing.

At step 170, once the tire rotation has stopped, the wheel clamping jaws of the lifting assembly are retracted. At step 175, the lifting assembly lowers the TWA back onto the base plate of the tire inspection station for conveyance by the conveyors 24, although the conveyors 24 are not started until a signal indicating the TWA is valid is received from a PLC or other controller, or a timeout occurs. Once the TWA is lowered back down, the lift assembly moves and/or rotates back to a pre-programmed neutral position (e.g. 0.5 degrees) under the base plate, so that the tire inspection station is ready for a next incoming TWA. In one or more preferred implementations, the system can repeatedly measure identical TWAs, or a series of different TWAs, with no impact on efficiency or accuracy.

The process waits at step 185 while the system processes and analyzes the tire sidewall images to determine if the detected data is valid, or until the system times-out.

Preferably, the laser imaging cameras 32,34 are 3D laser image cameras, and the images created by the laser imaging cameras 32,34 are "flattened" and "un-wrapped" images of the sidewalls of the tire. That is, preferably the system takes a curved image and renders it as a straight image as if the tire sidewall had been peeled off of the tire and straightened out. This results in a long rectangular image for image processing, which is much more accurate than attempting to process a curved or circular image.

Figure 12:
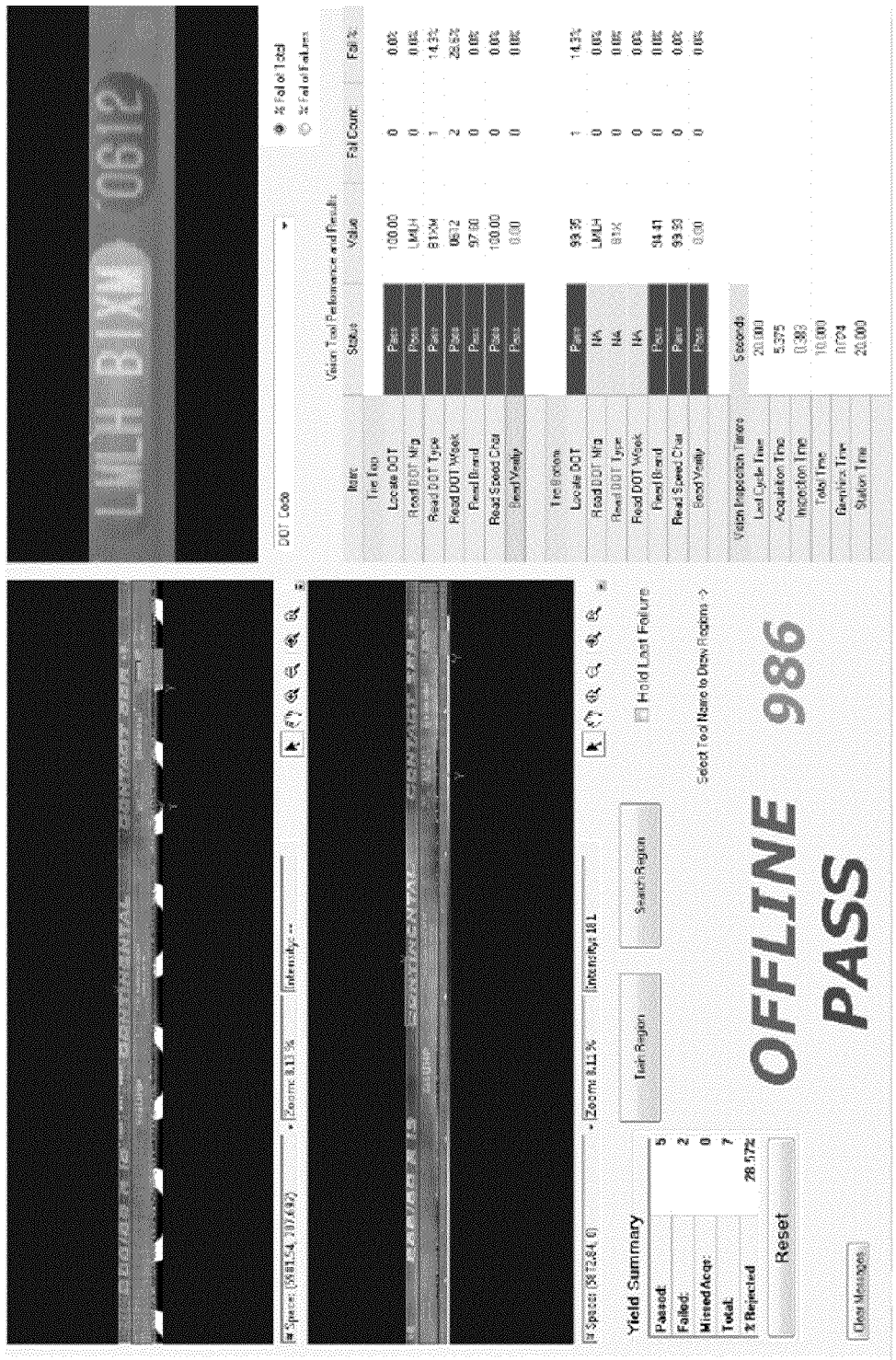
FIGS. 12-13 are exemplary interfaces of one or more applications in accordance with one or more preferred implementations.

FIG. 12 is an exemplary interface of an application in accordance with one or more preferred implementations which includes such "un-wrapped" images.

With the TWA mounted and the sidewall images captured, inspection can commence, and a tire inspection application loads the correct tire inspection program parameters for the detected TWA identification number from a TWA database.

Preferably, DOT information for various makes of tires will be trained beforehand. Once a particular tire is loaded into the tire station, the corresponding pattern, region and font files are loaded into the application memory.

In one or more preferred implementations, a pattern matching tool, such as PatMax® is utilized to compare a trained pattern to a pattern for a tire loaded in the tire inspection station.

The system first locates the DOT Codes using a pattern matching routine to find the raised or impressed letters and characters of the sidewall in the scanned sidewall images.

Upon finding a DOT pattern, the software draws three OCR search regions next to it which will span the characters of the DOT code. In one or more preferred implementations, locating a DOT pattern is important because other tools will operate based on the DOT location, and failure of this operation could cause other operations to fail.

Once the letters and characters of the DOT Codes are located, the location is used as a datum by the other optical character recognition (OCR) tools, such as those described herein. There are up to twelve (12) characters comprising the DOT Code string, which may be present as raised letters or otherwise. If any character is determined to be unreadable (or more likely, un-recognizable), a question mark (?) is inserted in the unread position. The first data point read using OCR is the tire manufacturer code, which comprises four characters. The second data point read is the tire type code, which comprises four characters, and the third data point is the manufacture date code, which is also four characters.

The OCR tools will try to read the characters in the given region based on the fonts trained for each particular OCR tool. If a particular character in the font library is missing or if the characters are molded badly, then an OCR tool may fail reading the characters.

Preferably, once a DOT code is read, pattern-matching techniques are utilized to analyze one or more scanned sidewall images to try and verify a tire brand and speed rating. Preferably, these tools work in the same way as the tool for locating a DOT pattern, except in that the trained patterns being used for comparisons are different. That is, the patterns that are trained for these tools will be the brand and speed ratings on the sidewall instead of DOT information.

Preferably, the system verifies that the DOT Codes are on the correct tire sidewall (top or bottom).

Following use of OCR tools, a bead verification tool is preferably utilized. Preferably, this tool operates to perform an inspection utilizing a blob tool to find dark areas in the sidewall of particular size and geometry. Unseated beads appear as dark blobs in the sidewall due to height differences from the camera.

Specifically, the process uses the imaging cameras 32,34 to determine whether the tire bead is properly seated on the wheel rim. If the tire is not seated properly, the sidewall surface on the unseated side of the wheel (either or both sides are possible) will be farther away from the imaging cameras 32,34. The 3D camera image will be very dark in the area where the bead is not seated. In one or more preferred implementations, the system is configured to use an imaging tool for a region located close to the bead seating area and determine whether there are a cluster of black pixels of sufficient size that would indicate a bad bead seat. The pass/fail status of this part of the inspection process is communicated to a PLC or other controller.

Preferably, the described inspections are executed on both sides of the tire and side verification of DOT presence is also performed. Once all inspections are executed, tool results are displayed in a results pane as illustrated in FIG. 12. In one or more preferred implementations, results or partial results are also overlaid on an image.

In one or more preferred implementations, system software returns a confidence score of between 1% and 100%. Preferably, the system is pre-loaded with a pass/fail criteria based on the confidence score.

Once the inspections have been executed, data corresponding to the results for that TWA is sent to a PLC or other controller.

If the system times-out or the data is determined to be invalid, the database is updated to assign a "failure" code to the TWA tracking number. On the other hand, if the data is determined to be valid, at step 190, the database is updated to assign a "pass" code to the TWA tracking number. Otherwise, a "fail" code is assigned to the TWA tracking number. The process then proceeds to step 195 where the TWA is ready for transfer to the wheel inspection station, and then proceeds to step 199 where the TWA is transferred to the wheel inspection station.

In one or more preferred implementations, the conveyors 24 and/or one or more other conveyors, such as conveyors 34, then move the TWA to the wheel inspection station 14, although in at least some implementations either inspection station may be a stand-alone system.

The wheel inspection station 14 comprises a 5 megapixel 2D camera and a large L.E.D. dome light. As a TWA is moving into the wheel inspection station, wheel inspection parameters are loaded from a database for that TWA. These can include, for example, proper trigger sensor position, camera exposure parameters, wheel pattern parameters, and color tool limits. The trigger sensor is moved to place an axis for the trigger sensor in an appropriate position to stop the TWA under the center of the dome light. That is, the trigger sensor is moved to a proper position for the specific TWA, allowing the TWA to be centered under the dome illumination assembly utilized which facilitates acquisition of a favorable image of the wheel. Thereafter, when a leading edge of the TWA breaks the axis for the trigger sensor, the TWA is stopped. Preferably, the PLC or other controller starts a wheel inspection process once the TWA has stopped in position at the wheel sensor.

In this process, a 2D camera records an image of the wheel at the proper exposure for comparison to a retrieved image for that wheel. The proper exposure (aperture and time) are retrieved from a database.

That image is then processed.

First, a wheel center hub of the wheel is located using a pattern matching algorithm. In one or more preferred implementations, this is accomplished using a PatMax® tool.

Next, the outside of the wheel rim diameter is detected by the camera by scanning from the hub outwards, and the outside diameter is located using multiple edge imaging tools. In one or more preferred implementations, this is accomplished via use of a circle find tool which uses multiple edge tools in a circular arrangement to locate the outer diameter.

Figure 13:
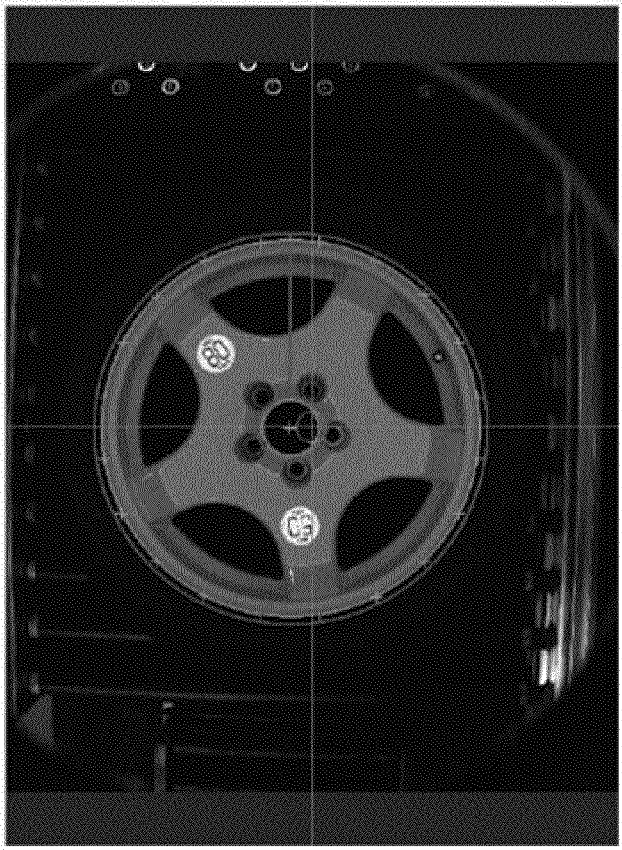

Using the two previous inspections of the wheel, the wheel image is "unwrapped" for wheel geometry processing. That is, the system takes the curved image and renders it as a straight image as if the wheel were flattened in a manner similar to a Mercator projection of a globe. Preferably, an annulus region is unwrapped to a rectangular region as illustrated in FIG. 13, which is a user interface of a wheel inspection application in accordance with one or more preferred implementations. This results in a long rectangular image for image processing, which is believed to facilitate accurate image processing as compared to trying to process a curved or circular image.

Using the hub center point and the outside rim diameter, the unwrapped region and "unwrapped" wheel spokes can be further analyzed by wheel geometry and wheel color tools.

Using a pattern matching algorithm, the specific wheel geometry (spoke design, etc.) is verified against retrieved data for the specific TWA identification number. Preferably, the geometric pattern of the wheel "spokes" is verified.

Using a histogram tool, the system also verifies wheel grayscale color. Preferably, the histogram tool verifies a grayscale value for the wheel color is between high and low limits. The low limit is preferably calculated by subtracting a low offset from a retrieved value learned during training for that wheel, and the high limit is preferably calculated by adding a high offset value to a retrieved value learned during training for that wheel.

The data from the wheel inspection station is then uploaded to a PLC or other controller for the wheel inspection station. The results from the wheel inspection station for the inspected TWA are then compared to a pass/fail criteria that is stored in a database. The conveying assembly is not started until a "data valid" signal is received from the PLC, or a timeout occurs. The TWA then proceeds on the conveying assembly to the output station 18.

As the TWA enters the output station 18, all the data from the input station 16, tire inspection station 12, and wheel inspection station 14 is transferred to the output station 18, and is indexed to the TWA tracking number. The conveying assembly can then be instructed as to the ultimate destination of the TWA. The TWA can be conveyed to an "inspected and accepted" queue, an "inspected and rejected" queue, or an "untrained" queue. The inspection data is permanently stored with the TWA tracking number.

A system in accordance with one or more preferred implementations is suitably enabled to allow a TWA to be present at each of the 4 stations simultaneously, as illustrated in FIG. 1, but can also process individual lot runs of a single TWA at a time if required or desired.

Aspects and features disclosed herein can be utilized in other systems as well. For example, in one or more preferred implementations, a subset of the components are utilized in a system, such as, for example, a system comprising a tire inspection station configured to operate independently which allows a tire manufacturer to inspect tires before shipment to a customer. Likewise, a system might comprise a wheel inspection station configured to operate independently which allows a wheel manufacturer to inspect wheels before shipment to a customer.

In one or more preferred implementations, it is possible to load a different TWA identification number into each of the four stations allowing a variety of TWAs to be quickly and efficiently inspected. This is facilitated by use of PLCs.

In accordance with one or more preferred implementations, 3D laser imaging cameras provide for accurate and repeatable TWA identification.

In one or more preferred implementations, a database of unique TWA identification numbers is utilized for an unlimited number of tire-wheel combinations.

By using a suitably enabled database of TWAs, it is possible to "teach' the system a large number of tire-wheel combinations that can then be used repeatedly. Notably, an unlimited number of tires can be combined with a particular wheel, and an unlimited number of wheels can be combined with a particular tire (in combinations—there will still be one tire and one wheel in each combination). In a similar manner, it is possible to "teach" a given tire, and the data captured can be used with multiple wheels with that tire. This makes it possible to "teach" wheels and tires separately, and then be able to inspect any combination of tire and wheel that is stored in the database. The use of servo positioning makes this practical.

By separating the tire inspection and wheel inspection applications from the user interface application, all applications run only as required and each application can be optimized on or for one or more PLCs.

In one or more preferred implementations, the use of two 3D laser imaging cameras for each tire sidewall makes it possible to provide an "unwrapped" rectangular image of both the top and bottom sidewalls. In one or more preferred implementations, the use of laser distance sensors allows a system to provide TWA size verification, automatic servo position training, and measurement and verification of tire height. In addition, the use of 3D laser cameras makes sidewall inspection practical and repeatable with a high degree of accuracy. However, servo positioning and the database loading of the precise positions required for the inspections allow the 3D laser cameras to achieve excellent results. In one or more preferred implementations, laser distance sensors facilitate automating what would otherwise be a difficult and cumbersome process of servo position training for each unique TWA. In one or more preferred implementations, laser distance sensors also provide safety and protection for a system itself by detecting incorrect or out-of-specification TWAs.

* * *

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A system comprising:
   (a) an input station configured to receive a tire wheel assembly;
   (b) a tire inspection station configured to inspect a tire of the tire wheel assembly, the tire inspection station comprising
      (i) a base plate comprising an opening therein,
      (ii) a plurality of rollers disposed in the base plate configured to facilitate movement of the tire wheel assembly across the base plate,
      (iii) one or more conveyors configured to translate the tire wheel assembly across the base plate,
      (iv) a lifting assembly configured to lift the tire wheel assembly disposed in the tire inspection station, the lifting assembly comprising a lift jaw mechanism configured to engage the tire wheel assembly for rotative movement thereof, the lifting assembly being configured to rotate an engaged tire wheel assembly about an axis of the lifting assembly,
      (v) first and second movable centering arms, the first and second movable centering arms being adjustably positionable relative to the base plate to center a hub of a tire wheel assembly relative to the lifting assembly for lifting of the tire wheel assembly,
      (vi) a top camera assembly disposed above the base plate, the top camera assembly including a 3D imaging camera and a laser distance sensor, and the top camera assembly being configured to translate horizontally along a first axis, and vertically along a second axis,
      (vii) a bottom camera assembly disposed below the base plate proximate the opening in the base plate, the bottom camera assembly including a 3D imaging camera and a laser distance sensor, and the bottom camera assembly being fixed vertically relative to the base plate but configured to translate horizontally along a third axis parallel to the first axis along an extent corresponding to the opening in the base plate;
   (c) a wheel inspection station comprising
      (i) one or more conveying assemblies configured to translate the tire wheel assembly,
      (ii) a dome illumination assembly comprising an opening disposed at a top thereof, (iii) a sensor configured to facilitate disposal of the tire wheel assembly under the dome illumination assembly via targeted stopping of translation of the tire wheel assembly by the one or more conveying assemblies,
      and (iv) a 2D camera;
   and (d) an output station;
   (e) a display screen; (f) one or more programmable logic circuits configured to control operation of the input station, output station, tire inspection station, and wheel inspection station;
   (g) wherein the system includes one or more non-transitory computer readable mediums collectively containing computer executable instructions for
      (i) receiving a particular tire wheel assembly at the input station,
      (ii) translating the particular tire wheel assembly from the input station to the tire inspection station,
      (iii) receiving a tire wheel assembly identification number and a tire wheel assembly tracking number for the particular tire wheel assembly,
      (iv) retrieving, based on the tire wheel assembly identification number, first configuration parameters,
      (v) positioning, based on the retrieved first configuration parameters, the first and second movable centering arms,
      (vi) translating, using the one or more conveyors, the particular tire wheel assembly forward over the lifting assembly, the centering arms effecting centering of the particular tire wheel assembly relative to a lifting axis of the lifting assembly,
      (vii) lifting, by the lifting assembly, the particular tire wheel assembly,
      (viii) effecting return of the first and second centering arms to a neutral position,
      (ix) translating the bottom camera assembly horizontally along the third axis and sampling distance measurements of the laser distance sensor of the bottom camera assembly during such translation,
      (x) effecting horizontal positioning of the bottom camera assembly at a position corresponding to a minimum distance measurement read during the translation of the bottom camera assembly horizontally along the third axis,
      (xi) effecting vertical positioning of the particular tire wheel assembly using the lifting assembly to dispose the particular tire wheel assembly a first set off distance from the bottom imaging camera, the first set off distance being based on the first configuration parameters,
      (xii) translating the top camera assembly horizontally along the first axis and sampling distance measurements of the laser distance sensor of the top camera assembly during such translation,
      (xiii) effecting horizontal positioning of the top camera assembly at a position corresponding to a minimum distance measurement read during the translation of the top camera assembly horizontally along the first axis,
      (xiv) effecting vertical positioning of the top camera assembly to dispose the top imaging camera a second set off distance from the particular tire wheel assembly, the second set off distance being based on the first configuration parameters,
(xv) engaging, by the lift jaw mechanism of the lifting assembly, the particular tire wheel assembly,
(xvi) rotating, by the lifting assembly, the particular tire wheel assembly four hundred degrees or more,
(xvii) imaging, by the top and bottom imaging cameras, top and bottom sidewalls of the particular tire wheel assembly during the rotation of the particular tire wheel assembly,
(xviii) rendering, based on data corresponding to the imaging by the top and bottom cameras of the top and bottom sidewalls during rotation of the particular tire wheel assembly, unwrapped images of the top and bottom sidewalls,
(xix) processing the unwrapped images, such processing including
  (1) locating one or more codes utilizing a pattern matching algorithm,
  (2) defining three optical character recognition search regions defined relative to the located one or more codes, and reading information from the defined optical character recognition search regions,
  (3) verifying that read information is on a correct tire sidewall,
  (4) determining whether there is a cluster of black pixels that would indicate a bad bead seat, and
  (5) generating one or more scores based on processing of the unwrapped images,
(xx) displaying, on the display screen, the unwrapped images and a results matrix including the generated one or more scores,
(xxi) disengaging, by the lift jaw mechanism of the lifting assembly, the particular tire wheel assembly,
(xxii) lowering, by the lifting assembly, the particular tire wheel assembly to the base plate,
(xxiii) returning the lifting assembly to a neutral position;
(xxiv) transferring the particular tire wheel assembly from the tire inspection station to the wheel inspection station,
(xxv) retrieving, based on the tire wheel assembly identification number, second configuration parameters,
(xxvi) positioning the sensor of the wheel inspection station based on the second configuration parameters,
(xxvii) translating the particular tire wheel assembly forward using the one or more conveying assemblies of the wheel inspection station,
(xxviii) detecting, using the sensor of the wheel inspection station, a leading edge of the particular tire wheel assembly as it is translated forward,
(xxix) in response to detecting the leading edge of the particular tire wheel assembly, ceasing forward translation of the particular tire wheel assembly such that it is disposed under the dome illumination assembly,
(xxx) imaging, by the 2D camera, the tire wheel assembly to produce a first image,
(xxxi) locating, in the first image, a wheel center hub using a pattern matching tool,
(xxxii) detecting, in the first image, an outside rim diameter using a circle find tool which utilizes multiple edge tools in a circular arrangement to locate the outer diameter,
(xxxiii) unwrapping, using data from locating the wheel center hub and data from detecting an outside rim diameter, an annulus region defined by such data to a rectangular region to produce a second image,
(xxxiv) comparing, using a pattern matching algorithm and the second image, specific wheel geometry of the particular tire wheel assembly to an ideal pattern,
(xxxv) verifying, using the second image, wheel color in grayscale,
(xxxvi) displaying, on the display screen, the first and second images and results based on the comparison of specific wheel geometry and the verification of wheel color.

2. The system of claim 1, wherein the first set off distance and the second set off distance are the same distance.

3. The system of claim 1, wherein the system comprises one programmable logic circuit for each station.

4. The system of claim 1, wherein the system comprises a single programmable logic circuit configured to operate all of the stations.

5. The system of claim 1, wherein the system comprises a plurality of programmable logic circuits.

6. The system of claim 1, wherein the system further comprises an input device.

7. The system of claim 1, wherein the system comprises a plurality of servos.

8. The system of claim 1, wherein lift jaw mechanism is configured to provide sufficient force so no slippage occurs during rotation of an engaged tire wheel assembly.

9. The system of claim 1, wherein the system further comprises one or more indicator lights.

10. The system of claim 1, wherein the system comprises greed and red indicator lights.

11. The system of claim 1, wherein the first set off distance and the second set off distance are different distances.

12. A method comprising:
  (i) receiving a particular tire wheel assembly at an input station,
  (ii) translating the particular tire wheel assembly from the input station to a tire inspection station,
  (iii) receiving a tire wheel assembly identification number and a tire wheel assembly tracking number for the particular tire wheel assembly,
  (iv) retrieving, based on the tire wheel assembly identification number, first configuration parameters,
  (v) positioning, based on the retrieved first configuration parameters, first and second movable centering arms,
  (vi) translating, using one or more conveyors, the particular tire wheel assembly forward over a lifting assembly, the centering arms effecting centering of the particular tire wheel assembly relative to a lifting axis of the lifting assembly,
  (vii) lifting, by the lifting assembly, the particular tire wheel assembly,
  (viii) effecting return of the first and second centering arms to a neutral position,
  (ix) translating a bottom camera assembly horizontally and sampling distance measurements of a laser distance sensor of the bottom camera assembly during such translation,
  (x) effecting horizontal positioning of the bottom camera assembly at a position corresponding to a minimum distance measurement read during the translation of the bottom camera assembly horizontally,
  (xi) effecting vertical positioning of the particular tire wheel assembly using the lifting assembly to dispose the particular tire wheel assembly a first set off distance from a bottom imaging camera of the bottom camera assembly, the first set off distance being based on the first configuration parameters, (xii) translating a top camera assembly horizontally and sampling distance measurements of a laser distance sensor of the top camera assembly during such translation, (xiii) effecting horizontal positioning of the top camera assembly at a position corresponding to a minimum distance measurement read during the translation of the top camera assembly horizontally, (xiv) effecting vertical positioning of the top camera assembly to dispose a top imaging camera of the top camera assembly a second set off distance from the particular tire wheel assembly, the second set off distance being based on the first configuration parameters, (xv) engaging, by a lift jaw mechanism of the lifting assembly, the particular tire wheel assembly, (xvi) rotating, by the lifting assembly, the particular tire wheel assembly four hundred degrees or more, (xvii) imaging, by the top and bottom imaging cameras, top and bottom sidewalls of the particular tire wheel assembly during the rotation of the particular tire wheel assembly, (xviii) rendering, based on data corresponding to the imaging by the top and bottom cameras of the top and bottom sidewalls during rotation of the particular tire wheel assembly, unwrapped images of the top and bottom sidewalls, (xix) processing the unwrapped images, such processing including
  (1) locating one or more codes utilizing a pattern matching algorithm,
  (2) defining three optical character recognition search regions defined relative to the located one or more codes, and reading information from the defined optical character recognition search regions,
  (3) verifying that read information is on a correct tire sidewall,
  (4) determining whether there is a cluster of black pixels of sufficient size that would indicate a bad bead seat, and
  (5) generating one or more scores based on processing of the unwrapped images, (xx) displaying, on a display screen, the unwrapped images and a results matrix including the generated one or more scores, (xxi) disengaging, by the lift jaw mechanism of the lifting assembly, the particular tire wheel assembly, (xxii) lowering, by the lifting assembly, the particular tire wheel assembly to a base plate, (xxiii) returning the lifting assembly to a neutral position below the base plate;

(xxiv) translating the particular tire wheel assembly from the tire inspection station to a wheel inspection station, (xxv) retrieving, based on the tire wheel assembly identification number, second configuration parameters, (xxvi) positioning a sensor of the wheel inspection station based on the second configuration parameters, (xxvii) translating the particular tire wheel assembly forward using one or more conveying assemblies of the wheel inspection station, (xxviii) detecting, using the sensor of the wheel inspection station, a leading edge of the particular tire wheel assembly as it is translated forward, (xxix) in response to detecting the leading edge of the particular tire wheel assembly, ceasing forward translation of the particular tire wheel assembly such that it is disposed under a dome illumination assembly, (xxx) imaging, by a camera, the tire wheel assembly to produce a first image, (xxxi) locating, in the first image, a wheel center hub using a pattern matching tool, (xxxii) detecting, in the first image, an outside rim diameter using a circle find tool which utilizes multiple edge tools in a circular arrangement to locate the outer diameter, (xxxiii) unwrapping, using data from locating the wheel center hub and data from detecting an outside rim diameter, an annulus region defined by such data to a rectangular region to produce a second image, (xxxiv) comparing, using a pattern matching algorithm and the second image, specific wheel geometry of the particular tire wheel assembly to an ideal pattern, (xxxv) verifying, using the second image, wheel color in grayscale, (xxxvi) displaying, on the display screen, the first and second images and results based on the comparison of specific wheel geometry and the verification of wheel color.

* * * * *